United States Patent [19]

Baldry et al.

[11] Patent Number: 5,109,805
[45] Date of Patent: May 5, 1992

[54] ABSORBENT MATERIAL

[75] Inventors: Michael G. C. Baldry; David A. Cummerson, both of Warrington, United Kingdom

[73] Assignee: Laporte Industries Limited, London, England

[21] Appl. No.: 689,891

[22] PCT Filed: Dec. 21, 1989

[86] PCT No.: PCT/GB89/01525
§ 371 Date: Jun. 12, 1991
§ 102(e) Date: Jun. 12, 1991

[87] PCT Pub. No.: WO90/07273
PCT Pub. Date: Jul. 12, 1990

[30] Foreign Application Priority Data

Dec. 24, 1988 [GB] United Kingdom ............... 8830266

[51] Int. Cl.$^5$ ............................................. A01K 67/00
[52] U.S. Cl. ................................................... 119/173
[58] Field of Search ....................... 119/171, 172, 173

Primary Examiner—Gene Mancene
Assistant Examiner—Thomas Price
Attorney, Agent, or Firm—Kane, Dalsimer, Sullivan, Kurucz, Levy, Eisele and Richard

[57] ABSTRACT

Small animal litter comprises an absorbent material containing an odor-reducing quantity of an aliphatic halo-nitro-bactericide such as those available under the Tradenames Bronopol, Bronidox or Myacide.

7 Claims, No Drawings

ABSORBENT MATERIAL

This invention relates to an absorbent material which may be used as a litter for, for example, household pets which may be small animals such as hamsters, gerbils, rabbits or, particularly, cats. The word "absorbent" is used in the colloquial sense and should not be understood to exclude adsorbent materials.

A wide variety of absorbent materials are suitable for use as litters and are available commercially as such. Such materials may be based on absorbent clays such as attapulgite or montmorillonite or may be based on calcium silicate or gypsum or even on cellulosic materials such as wood fibre or paper. In most cases such products are processed to render them particularly absorbent and resistant to physical degradation over a desirable period of use which will generally be at least 2 or 3 days and possibly up to 1 week.

A great problem for litter manufacturers has been the satisfactory masking or prevention of odour during the envisaged period of use. This is a particularly important aspect of a satisfactory litter product in the case of litter used in relation to cats.

A number of proposals have been made for the inclusion of fragrances or perfumes in litter products to mask odour. The present invention, however, relates to the prevention of odour generation at source.

It has been found that, while the mechanism of odour generation in litter may not be fully understood, odour may be abated over a reasonably extended period of use by the inclusion in the litter of a suitable bactericide or bacteriostat. Hereafter the term "bactericide" is used to include bacteriostats unless the context indicates otherwise.

U.S. Pat. No. 3,828,731 discloses a biodegradable litter material to which may be added, to inhibit the formation of odour-causing bacteria, benzaldehyde green ($C_{23}H_{25}ClN_2$), rose bengal, quaternary ammonium compounds or sodium or calcium propionate.

United Kingdom Patent Specification No. 1517124 discloses a litter material of prilled urea beads having a surface coating of calcium silicate containing a bactericide which may be quaternary ammonium salts, organic mercurial compounds, bisphenols, phenols or hexachlorophene.

U.S. Pat. No. 4,203,388 discloses a litter material made from recycled paper which may contain as a bactericide cetyl pyridinium chloride or cetyalkonium chloride.

United Kingdom Patent specification No. 2108389 discloses a biocidal composition, for addition to livestock litter, comprising an alkyl benzene sulphonic acid, where the alkyl group may contain from 4 to 20 carbon atoms, dissolved in a hydrophobic oil base.

European Patent Specification No. 109275 discloses a litter material which may comprise clay; such as kaolinite, montmorillonite or bentonite; fly ash; fibrous webs which may be cellulosic; or pelletised sawdust or polyurethane foam, the litter material also containing a broad spectrum bacteriostat which may be an alkyl monocarboxylic acid having from 3 to 9 carbon atoms or a halogenated aromatic hydrocarbon selected from halogenated phenols, halogenated disphenyls and halogenated bis-phenols. Specific examples of such halogenated aromatic hydrocarbon bacteriostats are p-chloro-m-cresol; hexachlorophene; 2,4,4'-trichloro-2'hydroxy phenyl ether; trichlorocarbanilide; 2,4-dichloro-m-xylenol; 3,4,5-tribromosalicylanilide; 3,5,3'4'tetrachlorosalicylanilide or others.

European Patent Specification No. 201209 discloses a litter material which may be a clay or synthetic calcium sulphate dihydrate containing a benzoic acid ester the ester moiety of which may contain 1 to 4 carbon atoms. Such esters are referred to as the "parabens".

According to the present invention there is provided a litter comprising an absorbent material containing a bactericidal additive the litter being characterised in that the additive comprises one or more aliphatic bromo-nitro-bactericides in which the bromo- and nitro- groups are carried on the same carbon atom.

A suitable class of bactericides for use according to the present invention is represented by the general formula:

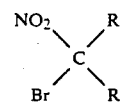

wherein R, in not more than one occurrence may represent a hydrogen atom, or in one or both occurrences represents an aliphatic or substituted aliphatic radical which preferably contains no more than 5 carbon atoms and/or in which, preferably, the substituent or substituents are halo-, for example bromo- or chloro-, and/or hydroxyl, alkoxy or alkylene dioxy radicals. Particularly preferred bactericides are:

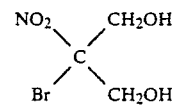

which is available in powder form under the Trade Name BRONOPOL-BOOTS (hereafter referred to as Bronopol) or in liquid form under the Trade Name MYACIDE or

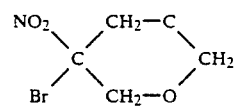

in which the aliphatic 2,2' substituted propyl chain is 1,3-substituted by a methylene dioxy diradical to form a ring structure, which is available under the Trade Name BRONIDOX L as a 10% weight active material in a liquid diluent.

The bactericides utilised in the practice of the present invention may be used in combination with normally difficult to disinfect absorbent bases such as recycled paper-based products and can be used with normally alkaline or only slightly acid absorbents despite being normally susceptible to deactivation under alkaline conditions. These bactericides also provide a useful and hitherto unknown alternative to the bactericides known for litter use such as the halogenated phenols, the quaternary ammonium compounds or the benzoic acid esters.

The applicant has found that known bactericidal activity is not necessarily an indication of effectiveness in a litter product since the presence and nature of the absorbent material exercises a considerable affect on bactericidal action. Thus, tests for bactericidal activity against bacteria added to, for example, cat's urine conducted in the absence of the absorbent can give a misleading impression of effectiveness and some bactericides which are effective under such conditions, may be relatively less effective in actual use in litter or may vary in effectiveness depending on the particular absorbent of which the litter is composed.

While the bactericides of the present invention appear to be effective in use in a wide range of absorbent bases the following are examples of absorbents particularly envisaged, either alone or in admixture with each other or with other materials.

(A) Clay Absorbents

These may be manufactured, for example, by the process disclosed in U.S. Pat. No. 4,657,881 according to which particles of a clay mineral containing some but not more than 15% by weight of water, and possibly containing additives, are compacted on a roller or static press into compacted masses which are broken down into the required litter particle size. The clays may be selected, for example from smectites, attapulgite and sepiolite and may very suitably be an alkali metal or alkaline earth metal montmorillonite available from Laporte Industries Limited under the Trade Name Surrey Powder.

Alternatively the clay may be for example a kaolinite, an attapulgite, a sepiolite or a montmorillonite, which has been screened to a suitable particle size, or agglomerated possibly with the addition of a binder without the use of high pressure. Such clays may have a lower moisture content or may have been calcined.

(B) Gypsum-based Absorbents

Gypsum (calcium sulphate dihydrate) forms the basis for a range of litter products. The raw gypsum is heated to form calcium sulphate hemihydrate which may alternatively be utilised as the preformed product "plaster". The hemihydrate is mixed with a controlled quantity of water to form a settable paste which, after setting and drying, is crushed and screened to the desired litter particle size. Such a process is described in U.S. Pat. No. 4,163,674.

(C) Cellulose-based Absorbents

There are many paper-based absorbents available for use as a litter base. Particularly, European Patent Specification Nos. 115898 and 169946 describe processes for the production of such a base by taking waste sludge from a paper mill having a content of cellulosic fibres of about 20% to 50% together with fillers, which sludge is dewatered to a semi-dry mass, granulated and dried.

(D) Calcium Silicate-based Absorbents

Such absorbents may be manufactured by the process described in, for example, United Kingdom Patent Specification No. 2039707 according to which a silicon dioxide such as quartz powder is reacted in an aqueous medium with calcium oxide and the product is moulded or shaped, autoclaved, comminuted, dried and graded.

(E) Polymeric Absorbents

A wide range of polymeric absorbents are known, many based on acrylate copolymers containing acid-functional groups cross-linked by the use of, for example vinyl polymers. One such range of polymeric absorbents suitable for litter use may be produced by the process disclosed in U.S. Pat. No. 4,342,858.

The above listed classes of absorbents represent a large proportion of the litter market. The listing is not intended to be limiting on the present invention, however, and other suitable absorbents may be used, such as for example peat or diatomaceous earth, alone or in admixture with the above.

The microflora of litter in use, which is thought to be responsible for at least some odour generation, may have to contend with a wide variety of conditions depending on the base selected as a result of the pH contribution of the base. Thus gypsum-based absorbents tend to have an alkaline pH, sometimes reasonably strongly alkaline, whereas natural clay absorbents tend to have a neutral or slightly acidic pH. Calcium silicate absorbents also tend to be reasonably alkaline, for example they may have a pH above 10, although there have been proposals, for example in European Patent Specification No. 66116, to reduce such pH by acid treatment into the 5.8–6.2 range. In use the litter will be subjected to urine having a pH approximately in the 5 to 8 range and the generation of ammonia by the microflora itself will tend to raise the environment into, or to maintain the alkaline state. It may be expected that, depending on the pH regime, a different balance between the various bacteria which may be responsible for odour may apply. The above considerations would lead to the selection of bactericide which is broad spectrum in action and is also effective in an environment which can be expected to be alkaline and possibly reasonably strongly alkaline.

The bactericides selected according to this invention have been associated with the belief that they are best suited to acid systems. At least in the case of "Bronopol" it has been reported that for cosmetic or pharmaceutical use adsorption of this bactericide onto powders that made the system alkaline would diminish antibacterial activity. (Soaps, Detergents, Toiletries Review 1978, 8(7) 29–30). It has further been reported in the same Journal (1978, 93(2) 47–48) that with the exception of non-alkaline systems, pH adversely affects the minimum inhibitory concentration of "Bronopol" against the bacterium *Escherichia coli* and that consequently such systems (alkaline systems) could not be adequately preserved. This last disclosure is highly pertinent to the present invention since the named bacterium is usually a substantial contributor to the in-use litter microflora. It has also been reported (Chemotherapy, Tokyo, 1974, 22(9) 1466–73) that the antibacterial spectra of "Bronopol" and "Chlorhexidine" (1,6 Bis (4-chlorophenyl, diguanadino-hexane) are not greatly different and that "Bronopol" is much inferior to chlorhexidine with regard to rapidity and strength of its bacterial effect. In the light of the above it may be surprising that, as will be shown hereafter, Bronopol has shown itself to be highly effective in its antibacterial effect both in relation to alkaline litters, and on a cost-equivalence basis in comparison with, for example, Chlorhexidine.

The quantity of bactericide which is included in the absorbent base according to the present invention is preferably at least an effective amount to achieve odour reduction over a normal period of use of litter of at least 1 day, particularly preferably from about 3 to 7 days. The quantity of bactericide used is preferably at least 0.008 g/kg of base and particularly preferably at least 0.01 g/kg of base. The upper end of the usage scale may be determined by cost considerations but it is usually necessary or cost effective not to use more than 2 g/kg of base. In practice a quantity of bactericide of about 0.05 to 1.2 for example, from 0.05 to 1.0 g/kg of base may prove to be suitable.

The method of including the bactericide in the absorbent base may be by mixing the base with the bactericide as available, whether in solid, liquid or solution form. Alternatively to simple mixing with, or absorbing onto, the litter the bactericide may be applied in a diluent such as polyvinyl alcohol which tends to form a surface film on the litter particles and therefore tends to retain the bactericide, to an extent at least, on the particle surfaces. If a solvent is used the litter product is preferably dried after treatment. In some cases it may be preferred to include the bactericide with the absorbent during the manufacture or particle-forming processes thereof. For example, the bactericide may be included with particle fines before compaction, or with particle agglomerates before crushing to the desired particle size. In general, however, a surface treatment of the finely formed litter is preferred.

In some instances the effectiveness of the bactericide may be increased by the inclusion of a surface active agent therewith. Such a surfactant may be non-ionic but is preferably anionic. A suitable quantity of surfactant is from 0.1 to 2.0 mg/kg of litter, preferably from 0.4 to 1.2 mg/kg of litter although smaller or larger quantities may prove effective. An example of a suitable non-ionic surfactant is TWEEN 80 (Trade Mark) and of a suitable anionic surfactant is sodium lauryl sulphate.

The absorbent according to the invention may include commonly used additives such as, for example, binders, colourants, perfumes, lubricants and the like in proportions known in the art.

The invention will now be described by reference to the following tests.

In the tests, unless otherwise stated, a given quantity of a bactericide was mixed into 16 g of absorbent base which was then contacted with 10 ml of standardised cat's urine and the mean cell count (cfu/ml) was determined at stated intervals.

Standardised urine was produced because some urines are found to be, of themselves, inhibitory to bacterial cell growth, possibly because of the previous treatment of the animals with antibiotics. The procedure was to screen urine samples for bacterial colony growth on agar after 2 days at 37° C. and, in the case of the samples which showed no appreciable growth under the above conditions, to test for inhibition of the growth, firstly, of *Escherichia coli* ATCC 11229 and if no inhibition were found, subsequently of *Pseudomonas aeruginosa* ATCC 15442, *Staphylococcus aureus* ATCC 6538 and *Streptococcus faecalis* ATCC 10541. The samples which showed no inhibition of any of these organisms were pooled and purposely contaminated with a standard low concentration of the four bacteria identified above.

In the following tests, the results of which are summarised in the Tables below, the following are details of the adsorbent bases used.

Calcium montmorillonite: A dried but uncalcined product available from Laporte Industries as SY410 (Trade Name)

Attapulgite: Available from Waverley Chemicals as LVM grade (calcined) pH 6.69

Calcium silicate: Available from Productos Dolometicos SA as Absorlite (Trade Name) pH 10.7

Cellulose: A paper mill effluent-derived product available from KNP Paper BV

Gypsum: pH 13.1

The quantities of bactericide were such as to equate approximately fo the same maximum material cost per liter of absorbent namely:

Bronopol: 1.05 g/kg
Cetyl pyridinium bromide: 3.0 g/kg
Chlorhexidine: 0.04 g/kg

Thus the tests are on a cost effectiveness basis and while a greater quantity of chlorhexidine might have given better results, the resulting material cost would be quite unacceptable commercially in a low value product such as litter.

TABLE 1

| Test No. | Absorbent base | Bactericide | Bacterial count after - hours/days | | | | | |
|---|---|---|---|---|---|---|---|---|
| | | | 5 h | 1 d | 2 d | 3 d | 4 d | 7 d |
| 1 | Ca montmorillonite | Bronopol | 3 | 1 | 3 | | 3 | |
| 2 | Attapulgite | Bronopol | 0 | 0 | | 0 | | 0 |
| 3 | | Cetyl pyridinium bromide | 1 | + | | ++ | | ++ |
| 4 | | Chlorhexidine | 15 | + | | ++ | | ++ |
| 5 | Ca silicate | Bronopol | 0 | 0 | | 0 | | 0 |
| 6 | | Cetyl pyridinium bromide | 10 | 0 | | 1 | | 1 |
| 7 | | Chlorhexidine | 2 | 2 | | 6 | | 8 |
| 8 | Cellulose | Bronopol | 0 | 0 | | 0 | | 7 |
| 9 | | Cetyl pyridinium bromide | 1 | + | | ++ | | ++ |
| 10 | | Chlorhexidine | 28 | + | | ++ | | ++ |

+ = >300.
++ = >1000.
hr = hour.
d = day.

The following tests were carried out using the same procedure as for Tests 1–10. The litter base was calcium montmorillonite (SY410) base. The quantities of bactericide are as stated and the cell count and other symbols have the same meaning as in Table 1.

TABLE 2

| Test No. | Bactericide | g/l | Bacterial count cfu/g in - hours/days | | | | | |
|---|---|---|---|---|---|---|---|---|
| | | | 1 hr | 5 hr | 1 d | 2 d | 3 d | 7 d |
| 11 | Chlorhexidine | 0.012 | 12 | 21 | ++ | | ++ | ++ |
| 12 | " | 0.12 | 5 | 14 | ++ | | ++ | ++ |
| 13 | Bronopol | 0.5 | | 1 | 1 | | 2 | 11 |
| 14 | Bronopol and Tween 80 | 0.05 0.625 | 2 | 3 | 74 | | ++ | ++ |
| 15 | As 14 but Bronopol and sodium lauryl sulphate | 0.625 | 18 | 1 | 1 | ++ | ++ | |
| 16 | Methyl paraben | 2.5 | 3 | 4 | + | ++ | | |
| 17 | " | 0.25 | 3 | 3 | + | ++ | | |
| 18 | " | 2.1 | 6 | 5 | + | ++ | | |

TABLE 2-continued

| Test No. | Bactericide | g/l | Bacterial count cfu/g in - hours/days | | | | | |
|---|---|---|---|---|---|---|---|---|
| | | | 1 hr | 5 hr | 1 d | 2 d | 3 d | 7 d |
| 19 | Cetyl dimethyl benzylammonium chloride | 0.21 | 8 | 5 | + | ++ | | |
| 20 | None | | 18 | 159 | + | ++ | | |

In tests 16 and 17 the methyl paraben was dissolved in polyvinyl alcohol and applied as a surface film to the litter particles. In tests 18 and 19 the bactericide was included in a CaCO₃ filler/polyvinyl alcohol composite and mixed into the litter.

In the following tests using the same procedure as for tests 1–10 the bactericide BRONIDOX was used in a quantity of 1.29 g/kg absorbents base which equated on a cost basis with the 1.05 g of BRONOPOL used above but represented a lower usage of active material. The base was varied as indicated in Table 3 below in which the cell count symbols have the same meaning as in Table 1.

TABLE 3

| Test No. | Absorbent base | Bacterial count cfu/g in ... days | | |
|---|---|---|---|---|
| | | 1 day | 2 days | 8 days |
| 21 | Ca montmorillonite | 23 | 19 | ++ |
| 22 | Attapulgite | 0 | 5 | 4 |
| 23 | Gypsum | 2 | 14 | ++ |
| 24 | Ca silicate (Absorlite) | 0 | ++ | ++ |
| 25 | Calciumsilicate (Calsilite) | 0 | 3 | 6 |
| 26 | Woodchip | 0 | 0 | 1 |
| 27 | Calsilite (BRONOPOL) | 0 | 0 | 0 |
| 28 | Woodchip (BRONOPOL) | 0 | 0 | 0 |

Tests 21, 22 and 24 show a poorer performance than the comparative tests using BRONOPOL (Tests 1, 2, 5) probably due to the smaller quantity of active material used. Nevertheless a useful performance was shown over 2 days and in the case of Test 22 over 8 days.

Tests 25 and 26 are comparative with Tests 27 and 28 in which latter tests 1.05 g/kg absorbent of BRONOPOL was used. They show that on some absorbent bases a useful performance may be obtained using only 0.129 g active material/kg of absorbent.

The following tests were carried out using the same procedure as for tests 1–10 using relatively low quantities of BRONOPOL and of the less costly MYACIDE on attapulgite and on calcium montmorillonite absorbent bases. The following results show that excellent results can be obtained at concentrations of bactericide at or below 0.5 g/kg absorbent base and that MYACIDE is at least as effective as BRONOPOL after a short initial period.

TABLE 4

| Test No. | Base | Bactericide | g/kg | cfu/g after | | | |
|---|---|---|---|---|---|---|---|
| | | | | 5 h | 1 d | 2 d | 3 d |
| 29 | Attapulgite | BRONOPOL | 0.53 | 0 | 0 | 0 | 1 |
| 30 | " | " | 0.26 | 5 | 23 | 33 | 49 |
| 31 | " | " | 0.11 | 10 | 44 | 44 | 31 |
| 32 | Ca. mont. | " | 0.53 | 0 | 0 | 0 | 3 |
| 33 | " | " | 0.26 | 1 | 12 | 49 | 46 |
| 34 | " | " | 0.11 | 53 | 55 | 70 | 101 |
| 35 | Attapulgite | MYACIDE BT | 0.53 | 0 | 0 | 0 | 0 |
| 36 | " | " | 0.26 | 0 | 20 | 39 | 13 |
| 37 | " | " | 0.11 | 44 | 47 | 46 | 14 |
| 38 | Ca. mont. | " | 0.53 | 0 | 1 | 11 | 0 |
| 39 | " | " | 0.26 | 12 | 31 | 35 | 56 |
| 40 | " | " | 0.11 | 50 | 40 | 23 | 63 |

In tests, in which a number of respondents judged the comparative odours emitted by samples of litter which had been treated with cat's urine a set period before, litter comprising calcium montmorillonite (SY410) treated with 1.05 g/l Bronopol showed a substantial reduction in odour in comparison with litter consisting of the same clay, without any addition of bactericide, and in comparison with some commercially available litters.

We claim:

1. Litter comprising an absorbent material containing a bactericidal additive the litter being characterised in that the additive comprises one or more aliphatic bromo- nitro-bactericides in which the bromo- and nitro- groups are carried on the same carbon atom.

2. Litter as claimed in claim 1 wherein the additive consists one or more of the compounds

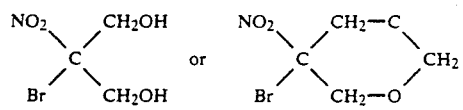

3. Litter as claimed in claim 1 wherein the absorbent material comprises one or more of clay-based, gypsum based, cellulose-based, calcium silicate-based or synthetic polymeric absorbent materials.

4. Litter as claimed in claim 1 wherein the quantity of the one or more halo- nitro-bactericides is at least 0.0008 g/kg absorbent material.

5. Litter as claimed in claim 4 wherein the said quantity is from 0.01 g/kg to 1.2 g/kg absorbent material.

6. Litter as claimed in claim 1 also containing one or more anionic or non-ionic surfactants.

7. Litter as claimed in claim 6 wherein the quantity of the one or more surfactants is from 0.1 to 2.0 mg/kg litter.

* * * * *